United States Patent [19]

Higley et al.

[11] 4,183,863
[45] Jan. 15, 1980

[54] CONVERSION OF CYCLOHEXANOL TO ε-CAPROLACTONE

[75] Inventors: David P. Higley, Katonah; Philip F. Wolf, Pleasantville, both of N.Y.

[73] Assignee: Union Carbide Corporation, New York, N.Y.

[21] Appl. No.: 897,511

[22] Filed: Apr. 18, 1978

[51] Int. Cl.$^2$ .................. C07D 313/04; C07C 179/08
[52] U.S. Cl. ..................................... 260/343; 568/567
[58] Field of Search ......................................... 260/343

[56] References Cited

U.S. PATENT DOCUMENTS

| | | | |
|---|---|---|---|
| 2,362,439 | 11/1944 | Ruzicka et al. | 260/343 |
| 2,462,337 | 8/1946 | Shechter | 260/343.5 |
| 3,428,656 | 2/1969 | Weiss et al. | 260/343 |
| 3,577,216 | 4/1971 | Weiss et al. | 260/526 R |
| 3,590,080 | 6/1971 | Beesley et al. | 260/343 |

OTHER PUBLICATIONS

Kortum et al., Pure and Applied Chemistry, vol. 1, Nos. 2-3, 1961, Dissociation Constants of Organic Acids in Aqueous Solution.

Primary Examiner—Alan L. Rotman
Assistant Examiner—Jane T. Fan
Attorney, Agent, or Firm—Bernard Francis Crowe

[57] ABSTRACT

Cyclohexanol is first autoxidized to a peroxide intermediate and then contacted with selenium dioxide catalyst and a base to afford ε-caprolactone.

8 Claims, No Drawings

CONVERSION OF CYCLOHEXANOL TO ε-CAPROLACTONE

BACKGROUND OF THE INVENTION

This invention pertains to the conversion of cyclohexanol to ε-caprolactone and more particularly to the stepwise autoxidation of cyclohexanol followed by conversion of the oxidation product to ε-caprolactone.

Lactones are used directly for the synthesis of polyesters, polyurethanes, and the like and indirectly for the production of lactams which are in turn converted to polyamides. Epsilon-caprolactone is a prime example of this class of lactones serving as a starting material for the production of poly-(epsilon-caprolactones), polyurethane elastomers and polyamides, such as, nylon-6. The synthesis of lactones in general and epsilon-caprolactone in particular has therefore been the subject of many research efforts.

The oxidation of cyclic ketones to cyclic lactones was discovered in 1899 and has since been known as the Baeyer-Villiger Reaction, although it has been broadened to include acyclic ketones. The oxidizing agents used in this reaction have included permonosulfuric acid (Caro's Acid), perbenzoic acid, monoperphthalic acid, peracetic acid and trifluoroperacetic acid. The selenium dioxide-catalyzed reaction of hydrogen peroxide with cyclic ketones to afford ring-contracted carboxylic acids was first reported in 1957 by G. B. Payne, et al., (J. Org. Chem., 22, 1680, 1957). In 1959 H. M. Hellman et al. reported in Tetrahedron Letters, 1 (1959) the formation of Baeyer-Villiger products, that is, cyclic lactones by employing selenic acid ($H_2SeO_4$) rather than selenium dioxide as the catalyst. However, they also obtained the ring-contracted carboxylic acids. Subsequent efforts to oxidize cyclic ketones up till the present time have afforded the same mixtures of cyclic ketones and ring-contracted carboxylic acid.

Commerically one of the most important applications of the oxidation of cyclic ketones to cyclic lactones is that of the conversion of cyclohexanone to epsilon-caprolactone. Japanese patent 6,910,243 (Chem Abstracts, 71, 60755a 1969) discloses the Baeyer-Villiger oxidation of cyclohexanone to epsilon-caprolactone using 30 percent aqueous hydrogen peroxide catalyzed by arsenic trioxide. An efficiency based on hydrogen peroxide of 74% was obtained and a conversion to the lactone of 64 percent. The Japanese patent No. 7007549 (Chemical Abstracts, 73, 14219x, 1970) describes the selenious acid ($H_2SeO_3$)-catalyzed oxidation of cyclohexanone with hydrogen peroxide at low temperatures, that is, less than 23° C. An efficiency of 11.2 percent to caprolactone based on 30 percent aqueous hydrogen peroxide was described together with a selectivity of lactone production of 58 percent.

It is believed that there are basically three methods of effecting the conversion of cyclohexanone to epsilon-caprolactone on a commercial scale. These are the direct oxidation of cyclohexanone with peracetic acid using ethyl acetate or acetone described in U.S. Pat. No. 3,522,279; the co-oxidation of aldehyde and cyclohexanone described in several references including Netherlands patent application No. 6,409,489 (Chemical Abstracts, 63, 8208f, 1965); and the oxidation of cyclohexanone with t-butyl hydroperoxide, catalyzed by boric anhydride, described in German Offenlegungschrift No. 2,253,963 (Chemical Abstract, 79, 456r, 1973).

While the above three described methods are commercial, they suffer in common the disadvantage of organic by-product formation. The economics of these processes are also dependent on the relative costs of the oxidants and their reduction products, viz., carboxylic acid from the first and second methods and t-butyl alcohol from the third method. This is especially significant in the case of the second method which at best produces nearly two moles of carboxylic acid per mole of epsilon-caprolactone.

Two variations of the first method described above have also been considered commercially, viz., the oxidation of cyclohexanone with peracetic acid using water as a solvent (Netherlands application No. 6,613,409; Chemical Abstract 67, 63845h, 1967) and the oxidation of cyclohexanone with aqueous performic acid (French patent 1,385,557; Chem. Abstracts, 62, 13051e, 1965).

These methods however also suffer the disadvantage of requiring the recycle of large amounts of carboxylic acids and the use of concentrated hydrogen peroxide.

There is therefore still a continuing need in this art for a method of synthesizing epsilon-caprolactone with a minimum of by-product formation.

SUMMARY OF THE INVENTION

It has now been found that ε-caprolactone can be synthesized in high yield by first oxidizing cyclohexanol to one or more peroxide intermediates, and then contacting said peroxide intermediate with a catalytic amount of a selenium compound having a valence of +4, selected from the group consisting of selenium dioxide, selenious acid, alkali metal salts of selenious acid, selenium halides, selenium oxyhalides, and dialkyl selenites having 1 to about 10 carbon atoms in each alkyl moiety, in the presence of at least about 0.1 equivalent weight, per equivalent weight of said selenium compound, of a base having a conjugate acid with a dissociation constant in the range of about $5 \times 10^{-8}$ to about $8 \times 10^{-2}$ at a temperature of about 20° to about 200° and preferably at a temperature of about 40° C. to about 100° C.

The term "halides" includes fluorides, chlorides, bromides and iodides.

The term "equivalent weight" is defined in the Condensed Chemical Dictionary 7th Edition, A. and C. Rose, Reinhold Publishing Corp., NYC 1966 as the weight that will combine with one atomic weight of hydrogen or replace one-half atomic weight of oxygen.

The term "conjugate acid" is defined in "Physical Organic Chemistry" by L. P. Hammett, page 48-49, McGraw Hill Book Co. NYC 1940.

In this sense a substance that acccepts a proton through an unshared pair of electrons is a base, and the product of the base plus a proton is an acid. The acid and base related this way are described as being conjugate or corresponding.

The cyclohexanol oxidation product is believed to be a complex mixture consisting mainly of 1,1'-dihydroxydicyclohexyl peroxide, and may also contain the following peroxides: 1-hydroperoxycyclohexanol, 1,1-dihydroperoxycyclohexane, 1-hydroxy-1'-hydroperoxydicyclohexyl peroxide, 1,1'-dihydroperoxydicyclohexyl peroxide, dicyclohexylidene diperoxide, tricyclohexylidene triperoxide, and the like.

Although it might appear more attractive to carry out the conversion of cyclohexanol to epsilon-caprolactone in one step, this is not feasible because the epsilon-caprolactone is unstable to the conditions required in the autoxidation of cyclohexanol.

The method used for oxidizing cyclohexanol to peroxide intermediates is not critical. Any conventional methods described in the chemical literature can be used including those described by N. Brown et al. J. Am Chem. Soc. Vol. 77, page 1756-9 (1955), E. G. E. Hawkins et al. in J. Chem. Soc. (C) pages 2691-7 (1966) and Chem. Abstracts Vol. 71, 38429a (1969).

While not wishing to be bound by any theory or mechanism of reaction, it is believed that this unexpected result is possible because the above-enumerated selenium compounds in the +4 valence state do not catalyze ring-contractive oxidation to by-products whereas selenium in the +6 valence state catalyzes both reaction routes, that is, leads to a mixture of both lactone and carboxylic acid by-product.

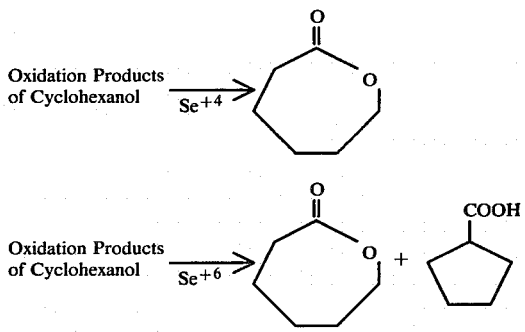

Selenium dioxide is the preferred catalyst for this reaction. The criticality of the catalyst is demonstrated by the fact that other selenium compounds such as selenic acid, diphenylselenide, diphenylselenoxide, benzeneseleninic acid and other selenium compounds do not afford the specificity of the +4 valence selenium catalysts enumerated above.

Suitable inert solvents include normally liquid aliphatic and cycloaliphatic ethers, benzene and its alkyl or halogen substituted derivatives and the like. A preferred cycloaliphatic ether is 1,4-dioxane.

The agent which has been discovered to inhibit the activity of selenium species in the +6 valence state can be generally described as a base although combinations of reagents which react to form weak bases can also be used, e.g., lithium selenite (dibasic) plus acetic, formic, or oxalic acids; alkali metal hydroxides such as lithium hydroxide plus acetic acid; alkali metal oxalates (dibasic) plus oxalic acid, and the like. The solubility characteristics of the additive in the reaction medium determine the effectiveness of the base in suppressing the activity of +6 selenium without inhibiting the activity of the selenium catalyst in the +4 state. Thus the combination of potassium oxalate and oxalic acid results in significantly lower reaction efficiency than that of lithium oxalate and oxalic acid, when 1,4-dioxane is used as a solvent. It is preferred to add the selenium compound in two portions for enhanced yields.

By catalytic amounts of a selenium compound is meant at least about 0.1 mole % of selenium compound based on the moles of cyclohexanol oxidation product.

Other bases which are effective include pyridine, piperidine, as well as other aromatic basic nitrogen-containing compounds. Aliphatic and cycloaliphatic nitrogen-containing compounds, such as, mono-, di-, and trialkylamines having 1 to 10 carbon atoms, cyclopentylamine, cyclohexylamine and N-substituted alkyl derivatives thereof can also be used. Still another variation is the use of basic ion exchange resins.

The use of a base to achieve the controlled reaction sequence described above is quite unexpected. The obvious expedient of using a reducing agent to keep selenium dioxide in the +4 valence state is unworkable because the selenium would be reduced down to selenium metal with 0 valence. Selenium in this valence state is not a catalyst for the conversion of cyclohexanol oxidation products to e-caprolactone.

The method of this invention can be practiced in a continuous or a batch system or a combination of both.

Pressure is not critical although atmospheric pressures are preferrred for reasons of economy.

Time is not critical. For practical yields reaction times of at least about one hour are preferred.

The invention is further disclosed in the Examples which follow. All parts and percentages are by weight unless otherwise specified.

EXAMPLE 1

AUTOXIDATION OF CYCLOHEXANOL

A 500 ml., creased reaction flask, fitted with a gas inlet tube, stirrer, thermometer and reflux condenser is charged with 280 g. of cyclohexanol and 2.8 g. of commercial cyclohexanone peroxide available from the Lucidol Division of Pennwalt Corporation, Buffalo, N.Y. Oxygen is passed into the reaction mixture with agitation while heating the flask to about 125° C. A product containing about 10 mole % oxidation product is obtained after about 10 liters of oxygen are passed into the reaction mixture. This is believed to be chiefly 1,1'-dihydroxydicyclohexyl peroxide.

CONTROL 1

CONVERSION OF 1,1'-DIHYDROXYDICYCLOHEXYL PEROXIDE TO EPSILON-CAPROLACTONE

A mixture of 3.45 grams (15 millimoles) of 1,1'-dihydroxydicyclohexyl peroxide, 41 mg. of selenium dioxide and 0.543 grams of chlorobenzene (internal standard for gas chromatographic analysis), in 20 ml. of dioxane (purified by distillation from sodium metal), was heated at 60° C. for 3 hours. Analysis of the product mixture by gas chromatography showed it to contain 5.2 millimoles of epsilon-caprolactone (35% of theory) and 3.7 millimoles of cyclopentane-carboxylic acid (25% of theory). The gas chromatographic analysis was conducted with a Carbowax 20 M column (a tradename of Union Carbide for ethylene oxide polymer having a molecular weight of about 20 thousand), with a column temperature programmed from 80 to 160°.

EXAMPLE 2

CONVERSION OF 1,1'-DIHYDROXYDICYCLOHEXYL PEROXIDE TO EPSILON-CAPROLACTONE IN THE PRESENCE OF PYRIDINE AS A BASE

Control 1 was repeated with the exception that a 0.12 gram portion of pyridine (1.5 millimoles) was added to the reaction mixture. The mixture was heated at 60° C. with stirring for 4 hours after which time an additional 41 mg. portion of selenium dioxide was then added and heating continued for 2 additional hours. Gas chromatogrphic analysis of the product mixture revealed it to contain 6.2 millimoles (41% of theory) of epsilon-caprolactone and 3.0 millimoles (20% of theory) of cyclopentanecarboxylic acid.

EXAMPLE 3

CONVERSION OF 1,1'-DIHYDROXYDICYCLOHEXYL PEROXIDE TO EPSILON-CAPROLACTONE IN THE PRESENCE OF LITHIUM HYDROXIDE/ACETIC ACID AS THE BASE

A mixture of 1.75 grams (7.6 millimoles) of 1,1'-dihydroxydicyclohexyl peroxide 20 mg of selenium dioxide, 64 mg of lithium hydroxide dihydrate, 100 microliters of glacial acetic acid, and 0.523 grams of chlorobenzene in 10 ml of dioxane was heated with stirring for 4 hours at 60° C. A second 20 mg portion of selenium dioxide was added after the first two hours of heating. Analysis of the product by gas chromatography showed the product mixture to contain 5.7 millimoles of epsilon-caprolactone (75% of theory) and 0.4 millimoles of cyclopentane carboxylic acid.

EXAMPLE 4

CONVERSION OF 1,1'-DIHYDROXYDICYCLOHEXYL PEROXIDE TO EPSILON-CAPROLACTONE IN THE PRESENCE OF LITHIUM OXALATE AND OXALIC ACID AS THE BASE

A reaction mixture consisting of 1.75 grams (7.6 millimoles) of 1,1'-dihydroxydicyclohexyl peroxide, 17 mg of selenium dioxide, 19 mg of oxalic acid, 16 mg of lithium oxalate (dibasic), and 0.523 grams of chlorobenzene in 10 ml of dioxane was heated with stirring for 3 hours at 60° C. A second 17 mg portion of selenium dioxide was then added and the mixture heated for 24 hours. Analysis by gas chromatography revealed the mixture to contain 6.5 millimoles of epsilon-caprolactone (85% of theory) and 0.8 millimoles of cyclopentanecarboxylic acid.

EXAMPLE 5

CONVERSION OF 1,1'-DIHYDROXYDICYCLOHEXYL PEROXIDE TO EPSILON-CAPROLACTONE IN THE PRESENCE OF LITHIUM SELENITE AS THE BASE

A reaction mixture cnsisting of 1.75 grams (7.6 millimoles) of 1,1'-dihydroxydicyclohexyl peroxide, 21 mg of lithium selenite (dibasic), 8.4 mg of selenium dioxide, 14 microliters of formic acid and 0.54 grams of chlorobenzene in 10 ml of dioxane was heated at 60° C. with stirring for 7.5 hours and left over night at room temperature. A second 8.4 mg portion of selenium dioxide was added and the mixture was heated at 60° C. for 3 additional hours. Analysis by gas chromatography revealed the product mixture to contain 6.7 millimoles of epsilon-caprolactone (89% of theory) and 0.6 millimoles of cyclopentanecarboxylic acid.

Although the invention has been described in its preferred forms with a certain degree of particularity, it is understood that the present disclosure of the preferred forms has been made only by way of example and that numerous changes may be resorted to without departing from the spirit and scope of the invention.

What is claimed is:

1. Method for the preparation of ε-caprolactone which comprises oxidizing cyclohexanol, and contacting the oxidized cyclohexanol with a catalytic amount of a selenium compound, having a valence of +4, selected from the group consisting of selenium dioxide, selenious acid, alkali metal salts of selenious acid, selenium halides, selenium oxyhalides, and dialkyl selenites having 1 to about 10 carbon atoms in each alkyl moiety, in the presence of at least 0.1 equivalent weights, per equivalent weight of selenium compound, of a base having a conjugate acid with a dissociation constant in the range of about $5 \times 10^{-8}$ to bout $8 \times 10^{-2}$, in an inert solvent whereby the oxidation by +6 valence selenium of said oxidation products of cyclohexanol is inhibited, at a temperature of about 20° C. to about 200° C.

2. Method claimed in claim 1 wherein the oxidized cyclohexanol is 1,1'-dihydroxydicyclohexyl peroxide.

3. Method claimed in claim 1 wherein the selenium compound is selenium dioxide.

4. Method claimed in claim 1 wherein the temperature is about 40° C. to about 100° C.

5. Method claimed in claim 1 wherein the selenium compound is charged in two portions.

6. Method claimed in claim 1 wherein the inert solvent is 1,4-dioxane.

7. Method claimed in claim 1 wherein the base is a mixture of lithium hydroxide and acetic acid.

8. Method claimed in claim 1 wherein the base is a mixture of lithium selenite and formic acid.

* * * * *